United States Patent [19]

Crossley et al.

[11] Patent Number: 4,728,658
[45] Date of Patent: Mar. 1, 1988

[54] PYRIDINE DERIVATIVES

[75] Inventors: Roger Crossley, Reading; Ian A. Cliffe, Burnham, both of England

[73] Assignee: John Wyeth & Brother Limited, Maidenhead, England

[21] Appl. No.: 771,949

[22] Filed: Sep. 3, 1985

[30] Foreign Application Priority Data

Sep. 5, 1984 [GB] United Kingdom ............... 8422461

[51] Int. Cl.$^4$ ............................................. A61K 31/44
[52] U.S. Cl. ............................... 514/354; 514/332; 514/344; 514/336; 514/337; 514/338; 514/339; 514/926; 514/927
[58] Field of Search .................... 514/354, 332, 344

[56] References Cited

U.S. PATENT DOCUMENTS 4,183,856  1/1980  Makisumi et al. ................. 546/306

FOREIGN PATENT DOCUMENTS 0069664   7/1982  European Pat. Off. .
154799   11/1980  German Democratic Rep. .
2047701  12/1980  United Kingdom ................ 514/354
539878    1/1977  U.S.S.R. .

OTHER PUBLICATIONS

Chemical Abstracts, 87, 5812x (1977).
Khim. Farm. Zh., 13, 46-9 (1979).
Chemical Abstracts, 91, 211217t (1979).
Fiziol. Akt. Veshchestva, 9, 17-19 (1977).
Chemical Abstracts, 88, 15765u (1978).
Gazz. Chim. Ital., 97, 135-147 (1967).
Chemical Abstracts, 67, 64364n (1967).
Rocz. Chem., 45(2), 250-9 (1971).
Chemical Abstracts, 75, 75600c (1971).
Chemical Abstracts, 86, 89560d (1977).
Chemical Abstracts, 66, 85680g (1967).

Primary Examiner—Frederick E. Waddell
Attorney, Agent, or Firm—George Tarnowski

[57] ABSTRACT

Pyridine derivatives having the formula I

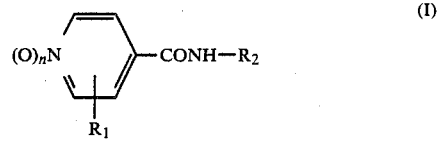

and their pharmaceutically acceptable salts (where n is 0 or 1; $R_1$ is hydrogen or lower alkyl and $R_2$ is an aromatic group) exhibit anti-secretory activity and may be used as anti-secretory agents and/or as anti-ulcer agents.

8 Claims, No Drawings

PYRIDINE DERIVATIVES

The invention relates to pyridine derivatives having pharmaceutical activity, particularly antisecretory activity. The invention also relates to pharmaceutical compositions containing the pyridine derivatives, processes for the preparation of the pyridine derivatives and methods of treatment of peptic ulcer diseases or gastric hypersecretion using the pyridine derivatives.

European No. 0,069,664A discloses compounds having general formula A

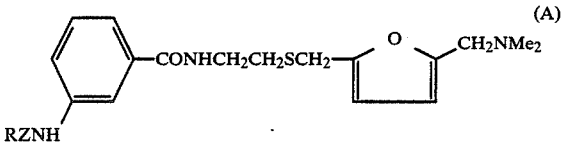

(where Z is CO or $SO_2$ and R is alkyl, phenyl, pyridyl, N-oxidopyridyl, pyrazinyl or thienyl) said to have antihistaminic activity. The compounds of general formula A include N-[3-[[[5-[(dimethylamino)methyl]-2-furanyl]methyl]thio]ethyl]amino]carbonyl]phenyl]-4-pyridinecarboxamide-1-oxide, which is the compound having formula A where R is 1-oxido-4-pyridyl and Z is CO.

3-[(1-oxo-4-pyridinylcarbonyl)amino]benzoic acid and 4-[(1-oxo-4-pyridinylcarbonyl)amino]benzoic acid which have formula B

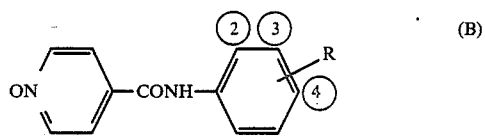

(where R is —$CO_2H$ is in the 3- or 4-position) and their methyl esters have been investigated for anti-inflammatory activity [Chemical Abstracts, 91, 211217t (1979) and 88, 15765u (1978)].

East German Patentschrift 0154 799 discloses that compounds having formula C

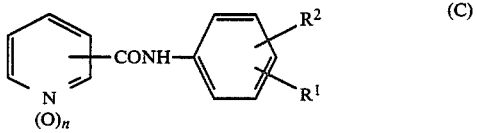

(where $R^1$ and $R^2$ are independently hydrogen, halo or alkyl and n is 0 is 1) are acaricides for control of plant pest mites. The specifically disclosed derivatives of pyridine-4-carboxamide-1-oxide are the N-phenyl, N-(2-chlorophenyl), N-(3-chlorophenyl), N-(4-chlorophenyl) and N-(4-bromophenyl) derivatives. The five compounds are of formula B where R is hydrogen, chlorine at the 2-, 3- and 4- positions respectively and bromine at the 4-position.

The present invention is based upon research to seek to find antisecretory activity in pyridine derivatives. The phenyl, 2-chlorophenyl and 4-chlorophenyl compounds mentioned in the last paragraph have been tested. The phenyl and 2-chlorophenyl compounds were not active. Surprisingly the 4-chlorophenyl derivative exhibited antisecretory activity. The inventors' studies have also shown that the chlorine atom may be replaced by other electron withdrawing substituents conventionally employed on aromatic rings.

The studies have also included the compounds of formula B where R is amino (—$NH_2$) in the 2-, 3- or 4- positions. The 3-amino and 4- amino compounds were inactive. Surprisingly the 2- amino compound exhibited antisecretory activity. Thus one aspect of the inventors' findings resides in the discovery that activity in the N-(phenyl)pyridine-4-carboxamide-1-oxide series requires one or more electron-withdrawing groups in the meta or para position and/or amino in the ortho position.

The present invention provides pyridine derivatives for use as antisecretory agents and/or as antiulcer agents. The pyridine derivatives are compounds having the general formula I

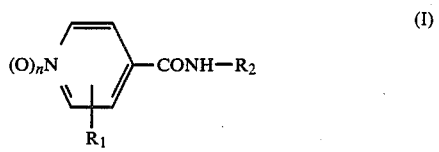

and their pharmaceutically acceptable salts. $R_1$ is hydrogen or lower alkyl. $R_2$ is (a) 2-aminophenyl, optionally substituted at other carbon atoms of the phenyl group by one or more substituents independently selected from "the class" consisting of halogen, trifluromethyl, nitro, cyano, monocyclic or bicyclic heteroaryl in which each of the heteroatom is a nitrogen atom, and groups having the formulae —O—Z—$OR_3$, —SO—$R_3$, —$SO_2$—$R_3$, —O—Z—$R_3$, —CO—$R_4$, —$CR_{5=NR_6}$, —$NR_7$—Z—$R_3$ and —Z—$R_8$ (where Z is —CO— or —$SO_2$—; $R_3$ is lower alkyl; $R_4$ is lower alkyl or aryl [for instance phenyl optionally substituted by halogen, $CF_3$, lower alkyl, lower alkoxy, di(lower alkyl)amino, nitro or cyano]; $R_5$ is hydrogen or the same as $R_4$ as defined above; $R_6$ is hydroxy or lower alkoxy; $R_7$ is hydrogen or —Z—$R_3$ where Z and $R_3$ are as defined above; and $R_8$ is the same as $R_6$ as defined above or —$NR_9R_{10}$ where $R_9$ and $R_{10}$ are independently selected from hydrogen or lower alkyl); (b) 3- or 4- (X) phenyl [where X is a substituent selected from "the class" defined above]; the 3- or 4- (X) phenyl group optionally being substituted at other carbon atoms of the phenyl group by one or more substituents independently selected from "the class" as defined above; (c) 2-[[(1-oxido-4-pyridinyl)carbonyl]amino]-4- (X)phenyl [where X is as defined above] optionally substituted at other carbon atoms of the phenyl group by one or more other substituents independently selected from "the class" defined above; and (d) monocyclic or bicyclic heteroaryl in which the or each heteroatom is nitrogen. The symbol n in formula I represents 1 or 0 subject to the proviso that n may be 0 only if $R_2$ has meaning (a).

The pyridine derivatives possess pharmaceutical activity, in particular antisecretory activity and hence are useful as antiulcer agents, in particular in the treatment of peptic ulcer disease, or for the treatment of gastric hypersecretion.

The pyridine derivatives are presented for the first time as pharmaceuticals except where $R_1$ is hydrogen whilst $R_2$ is 3- or 4- carboxyphenyl or the methyl ester thereof. The pyridine derivatives are novel per se except where $R_1$ is hydrogen whilst $R_2$ is 3- or 4- (halogen, carboxy or methoxycarbonyl)phenyl.

The invention particularly provides the pyridine derivatives having formula I and their pharmaceutically acceptable salts subject to the proviso that $R_2$ is not 3-(Y)phenyl or 4-(Y)phenyl where Y is halogen, carboxy or (lower alkoxy)carbonyl.

The term "lower" as used herein in respect of such groups as alkyl or alkoxy indicates that the group contains 1 to 6, preferably 1 to 4, carbon atoms. Thus "lower alkyl" includes methyl, ethyl, propyl, butyl and "lower alkoxy" includes methoxy, ethoxy, propoxy and butoxy. The term "halogen" as used herein contemplates fluorine, chlorine, bromine and iodine, preferably chlorine or bromine.

In formula I n preferably represents 1 but may also represent 0 where $R_2$ is optionally substituted 2-aminophenyl. $R_1$ is hydrogen or lower alkyl, preferably hydrogen, methyl or ethyl, advantageously hydrogen.

The preferred meanings of $R_2$ are groups having one of the formulae II, III, IV and V

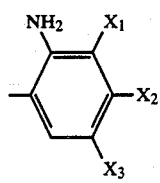

(II)

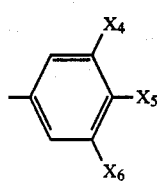

(III)

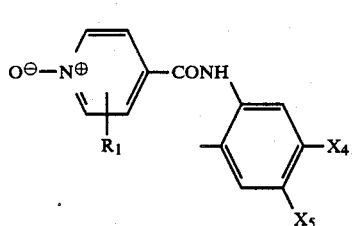

(IV)

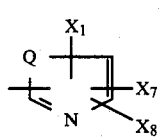

(V)

wherein $R_1$ is as defined above; Q is CH,N or —CH=CH—; $X_1$, $X_2$, $X_3$, $X_4$, $X_5$ and $X_6$ are independently selected from hydrogen and members of "the class" defined above subject to the proviso that at least one of $X_4$ and $X_5$ is not hydrogen and $X_7$ and $X_8$, when separate, are independently selected from hydrogen and members of "the class" defined above and $X_7$ and $X_8$, when joined together, represent —CH=CH—CH=CH— linked to two adjacent ring members of the ring shown in formula V.

The substituents that represent members of "the class" may be halogen for example, fluorine, chlorine, bromine); —CF$_3$; —NO$_2$; —CN; unsubstituted or substituted monocyclic or bicyclic heteroaryl groups containing nitrogen as each or the heteroatom [for example, pyridyl, pyrrolyl, imidazolyl, pyrazolyl, pyrazinyl, pyrimidinyl, pyridazinyl, tetrazolyl, indolyl, purinyl, quinolizinyl, isoquinolyl, quinolyl, phthalazinyl, naphthyridinyl, quinoxalinyl, quinazolinyl, cinnolinyl and pteridinyl which may be substituted, particularly by an electron withdrawing group such as halogen (for instance halopyridyl or 5-chloro-1-tetrazolyl)]; (lower alkoxy) carbonyloxy; (lower alkoxy)sulphonyloxy; (lower alkyl) sulphinyl; lower alkanesulphonyl; $C_2$–$C_7$ alkanoyloxy (e.g. acetoxy); lower alkylsulphonyloxy (e.g. methanesulphonyloxy); $C_2$–$C_7$ alkanoyl (e.g. acetyl); aroyl(e.g. benzoyl); 1-[(hydroxy or lower alkoxy)imino]$C_1$–$C_7$ alkyl; methyl substituted by aryl (e.g. phenyl) and (hydroxy or lower alkoxy)imino; mono- or di- ($C_2$–$C_7$ alkanoyl) amino (e.g. acetamido); carboxy; mono- or di-(lower alkylsulphonyl)amino; (lower alkoxy)carbonyl (e.g. methoxycarbonyl); carbamoyl optionally N-substituted by one or two lower alkyl groups; sulpho; (lower alkoxy)sulphonyl and sulphamoyl optionally N-substituted by one or two lower alkyl groups. Preferred members of "the class" include chlorine, bromine, nitro and trifluoromethyl.

Where the pyridine derivatives having formula I are basic or acidic in free form, the compounds of the invention include the pharmaceutically aceptable salts. For instance where $R_2$ contains carboxy (—CO$_2$H) or sulpho (—SO$_2$—OH), the compounds of the invention include pharmaceutically acceptable carboxylate or sulphonate salts which may be, for instance, alkali metal salts, particularly sodium or potassium salts, ammonium salts, alkaline earth metal salts such as calcium salts or salts of organic bases. Where $R_2$ is a basic group, for instance, 2-aminophenyl, the compounds of the invention include acid addition salts.

Examples of acid addition salts are those formed from inorganic and organic acids, in particular pharmaceutically acceptable acid addition salts such as the hydrochloride, hydrobromide, hydroiodide, sulphate, nitrate, phosphate, sulphonate (such as the methanesulphonate and p-toluenesulphonate) acetate, maleate, citrate, fumarate, tartrate, malonate and formate. The salts also include quaternary ammonium salts such as those formed from alkyl or aralkyl halides.

The compounds having formula I and their pharmaceutically acceptable acids may be prepared by a process that comprises (i) reacting a compound having the formula

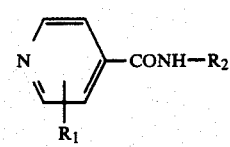

(VI)

(where $R_1$ $R_2$ are as defined above) with an oxidising agent to form the 1-oxide derivative; or (ii) reacting an amine having the formula $R_2$*NH$_2$ (wherein $R_2$* is the same as $R_2$ or a precursor therefor) or a reactive derivative thereof with a carboxylic acid having the formula

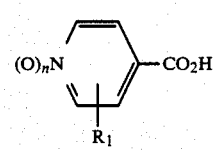

(VII)

or a reactive derivative thereof (where n and $R_1$ are as defined under formula I) and, where necessary, converting $R_2^*$ into $R_2$; or (iii) reducing a nitro compound having formula VIII

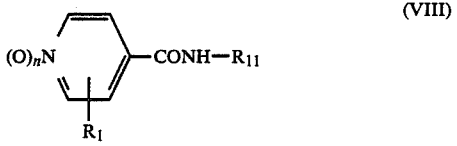

(VIII)

(where n is 1 or 0, $R_1$ is as defined above and $R_{11}$ is 2-nitrophenyl optionally substituted at other carbon atoms of the phenyl group by one or more substituents independently selected from "the class" as defined above) to convert the nitro group to amino.

Method (i) is for the preparation of compounds where n is 1 in formula I. The starting compound having formula VI may be prepared by reacting a carboxylic acid having the formula VIIa

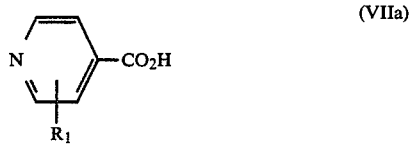

(VIIa)

(where $R_1$ is as defined above) or a reactive derivative thereof with an amine having the formula $R_2NH_2$ (where $R_2$ is as defined above). As oxidising agent for the oxidation of the starting compound having formula VI there may be used, for example, hydrogen peroxide, sodium periodate or a peroxyacid, for instance m-chloroperoxybenzoic acid. Where the compound to be oxidised contains optionally substituted 2-aminophenyl as $R_2$, the use of the m-chloroperoxybenzoic acid in an essentially stoichiometric amount is recommended because an excess of the oxidising agent may result in oxidation of the amino group.

Method (iii) identified above resides in the formation of amino by reduction of $-NO_2$. The nitro compound to be reduced is preferably prepared by reacting a carboxylic acid having formula VII or a derivative thereof with an amine $R_{11}-NH_2$ or a derivative thereof to form the amide linkage. The reduction is preferably carried out by catalytic hydrogen, by metal/acid reduction or by reduction in the presence of a hydrogen-donor, for instance, cyclohexene in the presence of a catalyst, for instance, palladium. Reductions involving dissolving a metal in acid may be used where the compound to be reduced contains no other function that may be reduced. Where another functional group present may also be reduced, conditions enabling selective reduction of only the $-NO_2$ group may be employed. In particular selective reduction of the $-NO_2$ group without, for instance, reduction of a 1-oxide-4-pyridyl group to 4-pyridyl, may be carried out by effecting catalytic hydrogenation until the theoretical uptake of hydrogen for the nitro group reduction has been achieved.

The method (ii) may be carried out by reacting the compound of formula VII with the compound of formula $R_2NH_2$ in the presence of a condensing agent, for instance, a carbodiimide. The use of 1,1'-carbonyldiimidazole as condensing agent is particularly recommended. Alternatively the acid of formula XIII may be reacted with a compound in which an amino function has been activated, for example, by forming the phosphazo derivative. The reactive acylating derivatives of the compound of formula VII may be employed, for example, active esters, acyl halides, simple or mixed anhydrides and the acid azide. The acid halides, particularly the acid chloride are especially suitable. The acylation product may be recovered from the reaction mixture by standard isolation procedures.

It will be apparent to those skilled in the art that certain unacylated compounds of formula $R_2NH_2$ may present more than one potentially reactive location for acylation.

For instance the compound of formula $R_2NH_2$ may be 1,2-benzenediamine or 4-halo-1,2-benzenediamine. In such cases as 1,2-benzenediamine the monoacylation product is a compound of the invention whilst the diacylation product is not. It has been found that the diacylation product may be formed where the molar ratio of diamine to acylating agent is about 1:1. To avoid the diacylation product the use of a substantial excess of the diamine reactant is recommended. In the case of such diamines as 4-halo-1,2-benzenediamine both the monoacylation product and the diacylation product are compounds of the invention. Should the monoacylation product be desired, diacylation may be avoided in the manner explained earlier, i.e. by using a substantial excess of the diamine reactant. However, monoacylation may lead to a mixture of monoacylation products as illustrated by the following reaction scheme

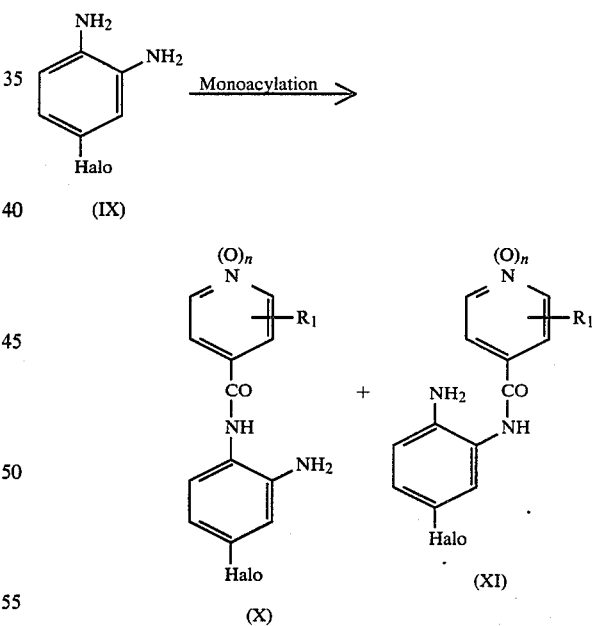

Where monoacylation leads to a mixture of monoacylation products, separation of the components of the mixture is required to recover individual products. Such a separation step is preferably avoided by making compounds such as x and XI in a different way, namely, by reducing a nitro group to form an amino group in accordance with method (iii) above.

Where the compound of the formula $R_2NH_2$ to be used in method (ii) contains an aldoxime or ketoxime substituent of formula $-CR_5=NOH$, this substituent may react under the acylating conditions. Normally the reaction is acylation so that the substituent is converted into the group having the formula XII

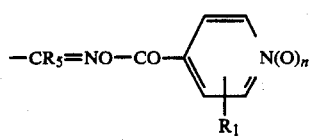

where $R_5$, $R_1$ and n are as defined above. The acyl derivative can be hydrolysed to restore the oxime substituent by means of aqueous alkali. Under the acylation conditions two other reactions may occur. If the conditions are acidic, a Beckmann rearrangement may occur to convert the oxime into an amide. Alternatively the substituent is of the formula —CH=NOH and acylation is carried out by means of vigorous treatment with the acid chloride or anhydride, dehydration can take place leading to the formation of a nitrile, i.e. —CH=NOH is converted into —CN. To avoid these two reactions we prefer to carry out the acylation by reacting the carboxylic acid of formula VII with the amine $R_2NH_2$ in the presence of a neutral condensing agent such as 1,1′-carbonyldiimidazole.

As an alternative to using the amine $R_2NH_2$ or a reactive derivative thereof, an amine having the formula $R_2^*NH_2$ or a reactive derivative thereof may be used in which $R_2^*$ is a precursor for $R_2$. The conversion of $R_2^*$ into $R_2$ is carried out as a step after the amide formation reaction. The conversion of $R_2^*$ into $R_2$ may be carried out by means of one or more known reactions. One important example has previously been mentioned. $R_2^*$ may represent, for instance, optionally substituted 2-nitrophenyl which is reduced to optionally substituted 2-aminophenyl as $R_2$. Other examples of possible aftersteps include:

(1) dehydration of —$CONH_2$ or —CH=NOH to form —CN;
(2) reaction of —$CR_5$=O with $HNR_6$ (where $R_5$ and $R_6$ are as defined above) to form —$CR_5$=$NR_6$;
(3) conversion of —Z—OH into —Z—O—lower alkyl or —Z—$NR_9R_{10}$ (where Z, $R_9$ and $R_{10}$ are as defined above) by reacting a reactive derivative of sulpho or carboxyl with a lower alkanol or with $NHR_9R_{10}$ (where $R_9$ and $R_{10}$ are as defined above); and
(4) formation of such heteroaryl groups as benzimidazolyl by cyclisation methods known per se for the ring formation.

Where a compound of the invention has the property of existing in free or salt form, the process of the invention may result in a compound of formula I or a salt thereof. A compound having formula I may be converted into a pharmaceutically acceptable salt by neutralization with an acid (if the compound having formula I is basic) or with a base (if the compound having formula I is acidic). A salt of a compound having formula I may be converted into a compound having formula I by addition of an acid (if the compound having formula I is acidic) or by addition of a base (if the compound having formula I is basic).

The invention includes a method of treatment of a subject in need of an anti-ulcer agent or an anti-secretory agent, which comprises administering an effective amount of a compound having formula I or a pharmaceutically acceptable salt thereof to the said subject.

Compounds of formula I may be tested for anti-secretory activity by their ability to inhibit the highly specific proton transporting enzyme $H^+/K^+$ ATPase.

Potential $H^+/K^+$ ATPase inhibitors are evaluated by a technique involving the measurement of aminopyrine accumulation in rabbit isolated gastric glands. Aminopyrine accumulates in acid-secreting cells; therefore, uptake of aminopyrine is increased by secretagogues and an inhibitor of acid secretion will reduce the response to one or more secretagogues depending upon its site of action. Compounds which reduce the response to dibutyryl cyclic adenosine monophosphate (DBcAMP) stimulation are assumed to have an intracellular site of action, and those which reduce the response to both DBcAMP and high potassium ion concentration ($K^+$) are thought to have an intracellular site of action at the secretory surface of the parietal cell, involving the highly specific proton transporting enzyme, $H^+/K^+$ ATPase.

The following test procedure is used:

Rabbit gastric glands are isolated from gastric mucosa from the corpus region of the stomach by a method based on one described by Berglindh T., Obrink K. J., Acta Physiol. Scand. 96, 150–159 (1976). Measurement of aminopyrine uptake is carried out using a procedure based on the method described by Berglindh T., Hellander H. F., Obrink K. J. (ibid. 97, 401–414, 1976).

Compounds are tested at a concentration of $10^{-4}M$, for their ability to inhibit $^{14}$C-aminopyrine uptake in gastric glands, stimulated by DBcAMP and high $K^+$ respectively. Results are expressed as the % inhibition of the maximum response to the secretagogue induced by the test compound.

In the above test the following compounds of formula I were active giving the results shown:

| Compound | % Inhibition to stimulation by: | |
|---|---|---|
| | DBcAMP | $K^+$ |
| N—(2-aminophenyl)pyridine-4-carboxamide-1-oxide | 106% at $10^{-4}$ M | 130% at $10^{-4}$ M |
| N—(4-nitrophenyl)pyridine-4-carboxamide-1-oxide | 33% at $10^{-4}$ M | 84% at $10^{-4}$ M |
| N—(4-chlorophenyl)pyridine-4-carboxamide-1-oxide | 22% at $10^{-4}$ M | 32% at $10^{-4}$ M |
| N—(2-aminophenyl)pyridine-4-carboxamide | — | 54% at $10^{-4}$ M |
| N—(3-chloro-4-trifluoromethylphenyl)pyridine-4-carboxamide-1-oxide | — | 168% at $10^{-4}$ M |
| N—(2-amino-4,5-dichlorophenyl)pyridine-4-carboxamide-1-oxide | — | 36% at $10^{-4}$ M |
| 4-chloro-N,N′—1,2-phenylenenebis(4-pyridinecarboxamide-1-oxide) | 20.5% at $10^{-4}$ M | 27% at $10^{-4}$ M |

The invention also includes pharmaceutical compositions containing a compound having formula I or a pharmaceutically acceptable salt thereof in association or combination with a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

The invention is illustrated by the following Examples:

EXAMPLE 1

N-(2-aminophenyl)pyridine-4-carboxamide-1-oxide

A mixture of 4-pyridinecarboxylic acid-1-oxide (2.2 g) and thionyl chloride (20 ml) was heated at reflux for 3 hours. Excess thionyl chloride was removed by evaporation and azeotroping with dichloromethane. The residue was suspended in dichloromethane (25 ml) and 1,2-benzenediamine (2.8 g) was added. The mixture was stirred at ambient temperature for 1 hour. Triethylamine (1.5 ml) was added and the mixture was stirred for 16 hours. The resulting solid was removed by filtration, washed with water and dried to give the title compound (3.3 g) m.p. 238°–9° C.

Analysis: Found: C, 62.4%; H, 4.9%; N, 18.1%. $C_{12}H_{11}N_3O_2$ requires C, 62.9%; H, 4.8%; N, 18.3%.

EXAMPLE 2

N-(2-pyridinyl)pyridine-4-carboxamide-1-oxide

A stirred suspension of 4-pyridine carboxylic acid-1-oxide (2.696 g, 19.4 mmol) in thionyl chloride (30 ml) was heated under reflux for 6 hours, cooled to room temperature, and evaporated in vacuo to give crude pyridine-4-carbonyl chloride-1-oxide as a solid from which excess thionyl chloride was removed as an azeotrope with dichloromethane.

A stirred suspension of the acid chloride in dichloromethane (50ml) at 0° was treated with 2-aminopyridine (1.823 g, 19.4 mmol), warmed to room temperature. After 3 hours the mixture was evaporated in vacuo to give a solid. The solid was dissolved in water (100 ml) and the solution basified with saturated aq. $Na_2CO_3$ solution. The precipitate was filtered and recrystallised from water to give the title compound as a three quarter hydrate (1.274 g), m.p. 232°–233°.

Analysis: Found: C, 57.6%; H, 4.6%; N, 18.1%. $C_{11}H_9N_3O_2.\tfrac{3}{4}H_2O$ requires C, 57.8%; H, 4.6%; N, 18.4%.

EXAMPLE 3

N-(2-benzimidazolyl)pyridine-4-carboxamide-1-oxide

A stirred suspension of 4-pyridine carboxylic acid-1-oxide (3.785 g, 27.2 mmol) in thionyl chloride (30 ml) was heated under reflux for 8 hours, cooled to room temperature, and evaporated in vacuo to give crude pyridine-4-carbonyl chloride 1-oxide as a solid from which excess thionyl chloride was removed as an azeotrope with dichloromethane.

A stirred suspension of the acid chloride in dichloromethane (50 ml) at 0° was treated with 2-aminobenzimidazole (3.988 g, 30 mmol), warmed to room temperature, and after 16 hours filtered. The precipitate was suspended in water (100 ml) and the mixture was basified with saturated aqueous sodium carbonate solution. The precipitate was filtered and washed with water (2×10 ml) and methane (3×30 ml). The precipitate was recrystallised from a mixture of dimethylformamide and water to give the title compound (2.343 g), m.p. 310°–314° (dec).

Analysis: Found: C, 61.0%; H, 4.15%; N, 21.5%. $C_{13}H_{10}N_4O_2$ requires C, 61.4%; H, 4.0%; N, 22.0%.

EXAMPLE 4

N-(4-chlorophenyl)-4-pyridinecarboxamide-1-oxide 1,1'-Carbonyldiimidazole (3.829 g, 23.6 mmol) was added to a suspension of 4-pyridinecarboxylic acid-1-oxide (2.986 g, 21.5 mmol) in dry dimethylformamide (50 ml) and the resulting solution was stirred for 45 minutes and treated with a solution of 4-chlorobenzenamine (3.012 g, 23.6 mmol) in dry dimethylformamide (20 ml). After 18 hours, the solution was evaporated in vacuo to give an oil which slowly solidified. The solid was recrystallised from ethyl acetate-cyclohexane and suspended in saturated aqueous sodium bicarbonate solution. The mixture was stirred vigorously for 20 minutes, filtered, and the crystals washed with water (3×10 ml) and ethanol (3×10 ml) and dried in vacuo to give the title compound as a quarter hydrate (1.614 g), m.p. 247°–249°.

Analysis: Found: C, 57.0%; H, 3.5%; N, 11.0%. Calculated for $C_{12}H_9ClN_2O_2.\frac{1}{4}H_2O$ C, 56.9%; H, 3.8%; N, 11.1%.

EXAMPLE 5

N-(2-aminophenyl)-4-pyridinecarboxamide

A stirred suspension of 4-pyridinecarboxylic acid (2.15 g, 17.5 mmol) in dichloromethane (40 ml) was treated with 1,1'-carbonyldiimidazole (3.115 g, 19.2 mmol) and the resulting solution was stirred for 85 minutes and added to 1,2-benzenediamine (3.777 g, 34.9 mmol) in dichloromethane (125 ml). After 3 hours, the precipitate formed was filtered and purified by chromatography ($SiO_2$; ethyl acetate) to give the title compound as pale yellow crystals (1.267 g), m.p. 225°–235°.

Analysis: Found: C, 67.8%; H, 5.2%; N, 19.4%. $C_{12}H_{11}N_3O$ requires C, 67.6%; H, 5.2%; N, 19.7%.

EXAMPLE 6

N-(4-nitrophenyl)pyridine-4-carboxamide-1-oxide 1,1'-Carbonyldiimidazole (4.939 g, 30.4 mmol) was added to a stirred suspension of 4-pyridinecarboxylic acid-1-oxide (3.848 g, 27.7 mmol) in dry dimethylformamide (50 ml). After 40 minutes, the resulting solution was treated with 4-nitrobenzenamine (4.203 g, 30.4 mmol), heated to 100°, and after 16 hours poured into water (200 ml). The precipitate was filtered, washed with water (3×50 ml) and methanol (2×15 ml), and recrystallised from ethanol-dimethylformamide (4:1) to give a first crop of product (0.692 g) as yellow crystals and a second crop of title compound (0.640 g) as yellow crystals, m.p. 280°–285° (dec).

Analysis: Found: C, 55.5%; H, 3.4%; N, 16.2%. $C_{12}H_9N_3O_4$ requires C, 55.6%; H, 3.5%; N, 16.2%.

EXAMPLE 7

N-(3,4-dichlorophenyl)-4-pyridinecarboxamide-1-oxide

A suspension of 4-pyridinecarboxylic acid-1-oxide (3.74 g, 26.9 mmol) and 1,1'-Carbonyldiimidazole (4.80 g, 29.6 mmol) in dry dimethylformamide (50 ml) was stirred for 40 minutes under an air-lock and treated with 3,4-dichlorobenzenamine (4.79 g, 29.6 mmol). The reaction mixture was heated at 100° for 5.3 hours and cooled to room temperature. The solution was evaporated in vacuo and the residue triturated with ethanol (80 ml) to give the title compound (5.38 g), m.p. 259°–265°.

Analysis: Found: C 50.8%; H, 2.8%; N, 10.3%. $C_{12}H_8Cl_2N_2O_2$ requires C, 50.9%; H, 2.9%; N, 9.9%.

EXAMPLE 8

N-[4-chloro-3-(trifluoromethyl)phenyl]-4-pyridinecarboxamide-1-oxide

A suspension of isonicotinic acid 1-oxide (4.16 g, 29.9 mmol) and 1,1'-Carbonyldiimidazole (5.33 g, 32.9 mmol) in dry dimethylformamide (50 ml) was stirred for 40 minutes under an air-lock and treated with 4-chloro-3-trifluoromethylbenzenamine (6.43 g, 32.9 mmol). The reaction mixture was heated at 100° for 5.3 hours and cooled to room temperature. The solution was evaporated in vacuo and the residue triturated with ethanol (2×20 ml) to give the title compound (5.379 g), m.p. 263°–265°.

Analysis: Found: C, 49.5%; H, 2.5%; N, 9.2%. $C_{13}H_8ClF_3N_2O_5$ requires C, 49.3%; H, 2.55%; N, 8.85%.

EXAMPLE 9

4-Chloro-N,N'-1,2-phenylenebis(4-pyridinecarboxamide-1-oxide)

A suspension of 4-pyridinecarboxylic acid-1-oxide (4.53 g, 32.6 mmol) and 1,1'-carbonyldiimidazole (5.81 g, 35.8 mmol) in dry dimethylformamide (50 ml) was stirred for 1 hour under an air-lock and treated with 4-chloro-1,2-benzenediamine (5.11 g, 35.8 mmol). The reaction mixture was heated at 100° for 18.5 hours, cooled to room temperature, and the precipitate filtered and washed with ethanol dimethylformamide and 2-propanone to give the title compound quarter hydrate (1.25 g), m.p. >300°. The compound exhibited infra-red spectral bands at 855, 1178, 1260, 1560, 1644, 1681, 3060, 3102, 3230 and 3299 cm$^{-1}$. The NMR spectrum of the compound in DMSO-$d_6$ exhibited the following signals (δ in ppm from TMS): double 1 proton doublet (J9 and 3Hz) at 7.33; 1 proton doublet (J9 Hz) at 7.67; 1 proton doublet (J3 Hz) at 7.79; 4 proton doublet (J7 Hz) at 7.93; 4 proton doublet (J7 Hz) at 8.36 and broad 2 proton signal at 10.2.

Analysis: Found: C, 55.6%; H, 3.45%; N, 14.3%. $C_{18}H_{13}ClN_4O_4.\frac{1}{4}H_2O$ requires C, 55.5%; H, 3.5%; N, 14.4%.

EXAMPLE 10

N-(2-amino-4,5-dichlorophenyl)-4-pyridinecarboxamide-1-oxide

A suspension of 4-pyridinecarboxylic acid-1-oxide (2.84 g, 20.4 mmol) and 1,1'-carbonyldiimidazole (3.64 g, 22.4 mmol) in dry dimethylformamide (50 ml) was stirred for 4 hours under an air-lock and the resulting solution added dropwise over 1 hour to a stirred solution of 4,5-dichloro-1,2-benzenediamine (7.23 g, 40.8 mmol) in dichloromethane (50 ml) under air lock. After 2.5 days, the mixture was evaporated in vacuo and the residue purified by chromatography [$SiO_2$; dichloromethane-methanoltriethylamine (100:3:1)]. Recrystallisation from ethanol-methanol gave the title compound (1.00 g), m.p. >300°. The compound exhibited infra-red spectral bands at 859, 1182, 1260, 1534, 1671, 3253, 3335 and 3417 cm$^{-1}$. The NMR spectrum of the compound in DMSO-$d_6$ exhibited the following signals: (δ in ppm from TMS) broad 2 proton signal at 5.5; 1 proton singlet at 6.97; 1 proton singlet at 7.42; 2 proton doublet (J7 Hz) at 7.96; 2 proton doublet (J7 Hz) at 8.37 and broad 1 proton singlet at 9.9.

Analysis: Found: C, 48.4%; H, 3.0%; N, 13.9%. $C_{12}H_9Cl_2N_3O_2$ requires C, 48.3%; H, 3.0%; N, 14.1%.

We claim:

1. A method of treatment of a subject in need of an anti-ulcer agent or an anti-secretory agent, which comprises administering an effective amount of a compound selected from those having the general formula I

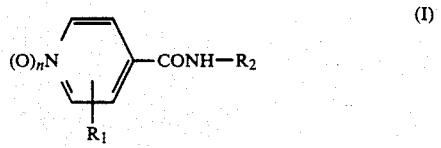

and their pharmaceutically acceptable salts, wherein $R_1$ is selected from hydrogen and lower alkyl; $R_2$ is selected from (a) 2-aminophenyl; (b) 2-aminophenyl substituted at one to three other carbon atoms of the phenyl group by a substituent independently selected from "the class" consisting of halogen, trifluoromethyl, nitro, cyano, and groups having the formulae $-O-Z-OR_3$, $-SO-R_3$, $-SO_2-R_3$, $-O-Z-R_3$, $-CO-R_4$, $-CR_5=NR_6$, $-NR_7-Z-R_3$ and $-Z-R_8$ (where Z is $-CO-$ or $-SO_2-$; $R_3$ is lower alkyl; $R_4$ is selected from lower alkyl and aryl; $R_5$ is selected from hydrogen, lower alkyl and aryl; $R_6$ is selected from hydroxy and lower alkoxy; $R_7$ is selected from hydrogen and $-Z-R_3$ where Z and $R_3$ are as defined above; and $R_8$ is the same as $R_6$ as defined above or $-NR_9R_{10}$ where $R_9$ and $R_{10}$ are independently selected from hydrogen and lower alkyl; (c) phenyl substituted by one to three substituents independently selected from "the class" defined above subject to the proviso that one such substituent is present at a position selected from the 3- and 4-positions of the phenyl group; and (d) 2-[[(1-oxido-4-pyridinyl)carbonyl]amino]phenyl substituted at the phenyl group by one to two substituents independently selected from "the class" defined above subject to the proviso that one such substituent is at the 4-position of the phenyl group; and n is selected from 1 and 0 subject to the proviso that where n is 0 then $R_2$ is selected from meanings (a) and (b).

2. The method as claimed in claim 1, wherein the compound is N-(4-chlorophenyl)-4-pyridinecarboxamide-1-oxide.

3. The method as claimed in claim 1, wherein the compound is N-(2-aminophenyl)pyridine-4-carboxamide-1-oxide.

4. The method as claimed in claim 1, wherein the compound is N-(2-aminophenyl)-4-pyridinecarboxamide.

5. The method as claimed in claim 1, wherein the compound is N-(4-nitrophenyl)pyridine-4-carboxamide-1-oxide.

6. The method as claimed in claim 1, wherein the compound is N-(3,4-dichlorophenyl)-4-pyridinecarboxamide-1-oxide.

7. The method as claimed in claim 1, wherein the compound is N-(4-chloro-3-(trifluoromethyl)phenyl)-4-pyridinecarboxamide-1-oxide.

8. The method as claimed in claim 1, wherein the compound is N-(2-amino-4,5-dichlorophenyl)-4-pyridinecarboxamide-1-oxide.

* * * * *